United States Patent [19]

Wagner

[11] Patent Number: 4,666,830
[45] Date of Patent: May 19, 1987

[54] ASSAY EMPLOYING SACS AND SAC LYSING AGENT

[76] Inventor: Daniel B. Wagner, 7705 Moorgate Ct., Raleigh, N.C. 27609

[21] Appl. No.: 643,478

[22] Filed: Aug. 23, 1984

[51] Int. Cl.$^4$ ............................................. G01N 33/53
[52] U.S. Cl. ............................................. 435/7; 435/4; 435/810; 436/501; 436/829
[58] Field of Search ............... 435/7, 4, 810; 436/829, 436/501

[56] References Cited

U.S. PATENT DOCUMENTS 4,483,921 11/1984 Cole .......................................... 435/7
4,517,303 5/1985 Freytag .......................... 436/829 X

*Primary Examiner*—Sidney Marantz
*Attorney, Agent, or Firm*—Elliot M. Olstein

[57] ABSTRACT

In an assay for an analyte, the tracer is comprised of a sac lysing agent, which lyses sacs containing detectable marker and sac lysing agent in inactive form which is activated when released from the sacs to provide a cascade effect which increases sensitivity.

24 Claims, No Drawings

ASSAY EMPLOYING SACS AND SAC LYSING AGENT

This invention relates to an assay for a ligand and products used in such assay. More particularly, this invention relates to an assay for a ligand in which the sensitivity of the assay is increased, as well as products used in such assay.

Immunoassay methods, in general, are based on the competition between a specific analyte, the amount of which is to be determined in a sample, and a known amount of the analyte or appropriate analog thereof in labeled form (tracer) for a limited number of available binding sites on a binder which is specific towards the analyte and tracer. Thus, in a system containing an unknown amount of analyte, a known amount of tracer and a limited known amount of binder, the greater the concentration of analyte in the sample, the less the tracer will be bound by the binder.

If the concentration of tracer and binder is fixed and the only variable is the level of analyte, it is possible to establish an assay system for measuring the unknown level of analyte by determining the amount of bound and free tracer in the system. Common labels include radioisotopes, fluorescent dyes, enzymes, chemiluminescent materials, and the like. The activity of the radioisotope, the fluorescent intensity of the dye or the activity of the enzyme on the substrate is compared with the values given by a range of known amounts of the analyte treated in the same manner. The values obtained from the determination of the standard samples are used for establishing a standard calibration curve for the specific system and this curve is then used to determine an unknown concentration of the analyte in a known sample.

In such assays, sensitivity is of prime importance, in that in many cases, it is necessary to measure low analyte levels.

In an attempt to provide more sensitive assays, tracers have been produced for use in the assay wherein the tracer is comprised of the analyte to be assayed or appropriate analog thereof coupled to a sac which includes a detectable marker therein. In such an assay, the amount of marker which can be included in the sac is greater than the amount of marker which can be directly linked to the analyte or appropriate analog thereof, whereby each mole of tracer has in excess of one mole of marker, which increases the sensitivity of the assay. In the case where the tracer is produced from a sac having a marker therein, which is sensitized with the analyte or appropriate analog thereof, there are still limits to the sensitivity in that, in general, only a single sac can be attached to each mole of the analyte or appropriate analog thereof. As a result, there is still a need for further increasing the sensitivity of an assay by amplifying the amount of detectable marker (per mole of analyte or appropriate analog thereof) used in formulating a tracer.

In accordance with one aspect of the present invention, there is provided an assay wherein one of the components used in the assay has an active sac lysing agent attached thereto, and another component in the assay is a sac, which has enclosed therein, a marker and sac lysing agent which is active for lysing sacs only when released from the sacs. In the assay, amplification is achieved by the active sac lysing agent coming into contact with at least one sac to release additional active sac lysing agent, as well as marker, with the release of active sac lysing agent resulting in the lysing of additional sacs, with the additional sacs releasing additional active sac lysing agent and marker, whereby there is an increase in the amount of marker released per mole of component used in the assay by a cascading effect.

More particularly, the assay is conducted in a manner such that the ligand having sac lysing agent coupled thereto (tracer) and analyte are contacted with a binder for at least the analyte. The ligand of the tracer is bound by one of the analyte and binder. The amount of tracer which is bound to the binder is dependent upon the amount of analyte in the sample (the analyte and tracer compete for binding sites on the binder or the tracer is bound to the binder through the analyte). The assay is effected in a manner such that tracer which is not bound to its binding partner (either analyte or binder) comes into contact with appropriate sacs, which sacs include therein a sac lysing agent in an inactive form, and detectable marker (in some cases, as hereinafter described, the sac lysing agent and detectable marker may be the same substance). As a result of such contact, the lysing agent attached to the tracer lyses the sac, thereby releasing marker and additional sac lysing agent which is activated when released from the sac. The released active sac lysing agent lyses additional sacs to release additional marker and additional active sac lysing agent to thereby increase the concentration of marker in the test medium. Since the amount of tracer available for lysing of the sacs is dependent upon the amount of analyte present in the sample, the amount of marker which is released after a specified time period, or the rate at which the marker is released, is indicative of the amount of analyte in the sample.

Thus, by proceeding in accordance with the present invention, each tracer molecule is capable of releasing a large number of marker molecules by a chain or cascading mechanism to thereby increase the overall sensitivity of the assay.

The sacs, which include a sac lysing agent and marker in the interior thereof, which are employed in the assay may be any one of a wide variety of sacs, which can be lysed by a sac lysing agent. Such sacs are generally known in the art, and include vesicles; in particular liposomes (lipid vesicles) (single walled or multi-lamellar), polymer microcapsules (for example, those made by coascervation, or interfacial polymerization), etc. As should be apparent, the sac employed in the assay is coordinated with the sac lysing agent attached to the ligand employed as tracer, as well as the lysing agent included within the sac, so that the sac is lysed or ruptured upon contact with the sac lysing agent. As hereinafter described, the sac lysing agent included within the sac is in an inactive form so that premature rupturing or lysing of the sac is prevented. The sac lysing agent included in the sac becomes active upon being released from the sac so that it is capable of lysing additional sacs.

Polymer microcapsules are produced by procedures known in the art, except that the solution in which the microcapsules are formed also includes a marker and sac lysing agent, whereby the interior of the polymer microcapsule includes the marker and lysing agent. The preparation of such microcapsules is disclosed for example in *Microencapsulation Processes and Applications,* edited by Jan E. Vandegger (Plenum Press 1974).

As known in the art, liposomes can be prepared from a wide variety of lipids, including phospholipids, glycolipids, steroids, relatively long chain alkyl esters; e.g., alkyl phosphates, fatty acid esters, e.g. lecithin, fatty amines and the like. A mixture of fatty materials may be employed such as a combination of neutral steroid, a charged amphiphile and a phospolipid. As illustrative examples of phospholipids there may be mentioned sphingomyelin, dipalmitoyl, lecithin, and the like. As representative steroids, there may be mentioned cholesterol, cholestanol, lanosterol, and the like. As representative examples of charged amphiphilic compounds, which generally contain from 12 to 30 carbon atoms, there may be mentioned mono-or dialkyl phosphate ester, e.g., dicetyl phosphate, dilauryl phosphate, dioctadecyl sulfonate, and the like.

The liposome sacs are prepared in an aqueous solution including the marker and sac lysing agent in an inactive form, whereby the sacs will include the marker and inactive sac lysing agent in the interior thereof. The liposome sacs are easily prepared by vigorous agitation in the solution, followed by removal of the marker and inactive sac lysing agent from the exterior of the sac. Other preparation methods may also be employed.

Further details with respect to the preparation of sacs are set forth in U.S. Pat. No. 4,342,826 and PCT International Publication No. WO80/01515, as well. "Liposomes: From Physical Structure to Therapeutic Applications," C. G. Knight, Ed. Elsevier, 1981, and "Membrane Mimetic Chemistry" by Janos H. Fendler. John Wiley and Sons, 1982 all of which are hereby incorporated by reference.

As hereinabove indicated, the sac lysing agent, which is included in the sacs, must be in an inactive form so as to prevent premature ruturing of the sacs, and the sac lysing agent must be in an active form when released from the sacs. Thus, for example, when using an enzyme as a sac lysing agent, the enzyme lysing agent may be maintained inactive within the sac by encapsulating the enzyme within the sac in the absence of an essential metal ion, such as calcium. This may be accomplished by use of a calcium complexing agent, such as ethylene diamine tetraacetate (EDTA), and in the absence of calcium, the enzyme lysing agent will not lyse the sac. Upon releasing the inactive form of the enzyme lysing agent (absence of calcium) into a calcium rich solution, the lysing agent will be activated and capable of lysing other sacs.

The sac lysing agent may be any one of a wide variety of materials which is capable of lysing the sac employed in the assay, with the particular sac lysing agent employed being dependent upon the sacs employed in the assay. The preferred lysing agent is an enzyme, and the enzymes capable of lysing different sacs would be known to those skilled in the art. Thus, for example, phospholipases are suitable enzymatic lysing agents, and may be inactivated by use of a calcium complexing agent such as EDTA. A protease enzyme is known to be effective for lysing a gelatine microcapsule.

As hereinabove indicated, the lysing agent which is included in the sac must be in an inactive form so as to prevent premature lysing or rupturing of the sac. In accordance with a preferred embodiment, an inhibitor is included within the sac in an amount which would inhibit the enzymatic activity of the lysing enzyme within the sac, and which when diluted by the assay medium, would not inhibit the lysing action of the lysing enzyme. As hereinabove indicated, EDTA may be used for inactivating a calcium dependent enzyme. A representative concentration for EDTA (to inhibit a calcium-dependent enzyme) is 1 to 10 mM. The entrapped volume of the liposome is very small compared to the total assay volume, so that on lysis, the inhibitor becomes highly diluted (dilution factor may be in the range of 1:1000 to 1:100,000 or even more). The inhibitor, being water-soluble, is encapsulated in the same manner at the same time as the enzyme and the marker. Another method of inactivation is by removing the so-called co-enzyme by known techniques. The apoenzyme thus obtained is encapsulated, and the co-enzyme is kept in solution outside the liposomes. On lysis, the encapsulated enzyme, which is in the apoenzyme inactive form, combines with the co-enzyme to form an active enzyme.

The marker which is included within the sac may be any one of a wide variety of detectable markers, including but not limited to, radioisotopes, enzymes (in the use of an enzyme, the marker and lysing agent may be the same enzyme, or may be different enzymes), a chromogen (an absorbing dye or a fluorescent material), a luminescent compound, a phosphorescent compound, spin labels, etc. Such detectable markers, and the methods for determining the markers are generally known in the art, and no further details in this respect are deemed necessary for a complete understanding of the invention. The preferred types of markers to be employed are:

a. Dyes with a high extinction coefficient, such as sulforhodamine B copper phthalocyanine tetrasulfonic acid, oxazine 4 perchlorate.

b. Fluorescent dyes, such as carboxyfluorescein, organic chelates of europium and terbium, various coumarins and rhodamines.

c. Enzymes other than the lysing enzymes, such as horseradish peroxidase, which can be determined, after lysis, by a colorimetric, fluorescent, luminescent, or electromechanical (amperometric) device.

As hereinabove indicated, the tracer which is employed in the assay is a ligand having a sac lysing agent in an active form, coupled thereto. The sac lysing agent is of a type as hereinabove described. The ligand which is employed in producing the tracer is dependent upon the assay which is employed. Thus, for example, if the assay is for an analyte which is an antigen or a hapten, the ligand portion of the tracer may be the analyte or appropriate analog thereof.

As used herein, the term "appropriate analog", when referring to an analog of the analyte, means that the analog of the analyte is bound by the binder for the analyte which is used in the assay. If the analyte is an antibody, the ligand portion of the tracer may be an antigen bound by the antibody or an antibody elicited in response to the analyte.

The ligand portion of the tracer is bound by one of the binder or the analyte. Thus, for example, in a so called "sandwich" assay, the analyte may be bound by the binder and the tracer bound by the analyte, whereby the amount of tracer bound to the binder through the analyte is dependent on the amount of analyte in the sample.

The above types of assays and others should be apparent to those skilled in the art from the teachings herein.

The ligand portion of the tracer may be coupled to the lysing agent by procedures which are generally known in the art for coupling one compound to another. Thus, for example, the lysing agent may be coupled to the ligand portion of the tracer by covalent coupling, derivitization, activation, and the like.

The lysing agent may be coupled to the ligand portion of the tracer by the use of an appropriate coupling or spacer compound (one that does not destroy the immunoreactivity of the tracer, or the sac lysing activity of the lysing agent). As known in the art, the coupling compound has two reactive functional groups, one of which functional groups is capable of reacting or being linked to a functional group of the ligand portion of the tracer, and the other of which is capable of reacting or being linked to a functional group on the sac lysing agent. For example, the spacer or coupling compound, which includes at least two reactive substituent groups, may contain either a carboxyl, isocyanate, isothiocyanate, amino, thiol, hydroxy, sulfonyl, carbonyl, etc., substitutuent group, which, as should be apparent, is dependent upon the functional group present in the ligand and lysing agent which are to be coupled to each other.

Alternatively, the sac lysing agent may be coupled directly to the ligand. Thus, for example, if the ligand portion of the tracer has an amino substituent group, and the sac lysing agent portion of the tracer has a carbonyl or carboxyl substituent group, then the ligand and sac lysing agent may be directly conjugated to each other by procedures known in the art; for example, an active ester technique.

The binder which is used in the assay is one which is specific for the analyte. In the case where the analyte is an antigen or a hapten, the binder may be an antibody or a naturally occurring binder which is specific for the analyte. In the case where the analyte is an antibody, then the binder employed in the assay may be either an antigen or an antibody elicited in response to the antibody to be assayed, whereby the binder is specific for the analyte.

As hereinabove indicated, the assay is effected in a manner such that tracer which is not bound to the binder comes into contact with sacs which include both the sac lysing agent in an inactive form and the detectable marker, and this may be conveniently accomplished by supporting the binder on a solid support, whereby bound tracer is not free to move through the assay medium to thereby contact the sacs employed in the assay.

Thus, for example, the binder may be supported on a solid surface by procedures known in the art, including absorption, covalent coupling, activation, etc. The solid support for the binder may be any one of a wide variety of solid supports which do not interfere with the assay, including, but not limited, to polymer supports, such as polypropylene, polystyrene, polyethylene, etc.; glass, bacterial cells; ion exchange resins, etc. Such solid supports are known in the art and no further details in this respect are deemed necessary for a full understanding of the invention.

As known in the art, the solid support may be in a wide variety of forms, such as a test tube, a sheet or plate, solid particles, etc.

It is also to be understood that the binder may be employed in the assay in an unsupported form, with the bound and free portions being separated from each other prior to contacting the free tracer with the sacs.

In employing a solid supported binder, in some cases, it may be necessary to separate the supported binder having tracer bound thereto, prior to contacting the unbound tracer (free tracer) with the sacs which include in the interior thereof the marker and sac lysing agent in an inactive form.

In other cases, for example, when the binder is supported on the walls of a tube, the bound tracer is not free to move in the assay media and, accordingly, it may not be necessary to separate the free tracer from the bound tracer, prior to contacting the free tracer with the sacs of the type hereinabove described.

In employing a supported binder, it may be possible to incubate the sample containing the analyte (ligand to be assayed), and the tracer in the presence of a supported binder in an assay medium including the sacs containing both the detectable marker and the sac lysing agent in an inactive form. In such a procedure, the rate of lysing is a function of the concentration of the free tracer in that the bound tracer does not freely move through the assay medium. Although the sacs are free to move in the assay medium, and are therefore theoretically free to move into contact with bound tracer to initiate lysing of the sacs by bound tracer, as a practical matter, the probability of such an event is believed to be small whereby the lysing rate of the sacs is a function of the concentration of free tracer in the assay medium. In some cases, it may be advantageous to add the sacs after the initial incubation to form the free and bound tracer fractions, or in the alternative, to separate the free fraction from the bound fraction, and then contact the free fraction with the sacs including both the detectable marker and the sac lysing agent in an inactive form.

The assay of the present invention may be employed for determining a wide variety of analytes, and has particular applicability to those analytes which are generally found in low concentrations in the material to be assayed. As representative examples of such analytes, there may be mentioned: Cardiac glycosides, such as digoxin and digitoxin. Antiasthmatics, such as theophyllin. Anitbiotics, such as gentamicin and tobramycin. Antineoplastics, such as methotrexate. Anticonvulsants, such as phenobarbital, carbamezapine and valparic acid. Antiarrythmics, such as lidocaine and quinidine. Hormones, such as T4, T3, hCG, TSH, and various steriods. The invention is not limited to the representative examples.

In accordance with one aspect of the assay of the present invention, a sample containing or suspected of containing the analyte is incubated with a tracer, which is the analyte or appropriate analog thereof coupled to a sac lysing agent, and a binder specific for both the analyte and tracer. The incubation results in competition between the tracer and analyte for binding sites on the binder, with the amount of tracer which is bound to the binder being inversely proportional to the amount of analyte in the sample.

The bound and free components are separated from each other, and the free portion is then contacted with sacs, which include both marker and sac lysing agent in an inactive form therein, under conditions which prevent premature rupturing of the sacs (the sacs are only ruptured by contact with lysing agent which is exterior to the sacs). This portion of the assay is generally run in an appropriately buffered aqueous medium which is isotonic with the osmolarity of the sacs. Thus, conditions of temperature, pH and ionic concentration are controlled to prevent premature rupturing of the sacs. Thus, for example, an aqueous buffered medium is provided which is isotonic with the osmolarity of the sacs. In general, the buffer provides a pH in the order of from 5 to 9.

As a result of the contact with the lysing agent portion of the tracer, the sacs are ruptured to release additional lysing agent and marker with the released lysing agent being in an active form (for example, the assay medium includes calcium, whereas the interior of the sac includes a calcium inhibitor). The release of active lysing agent produces a cascading or amplification effect, as hereinabove described. The rate at which marker is released into the medium is dependent upon the concentration of tracer present, with an increasing amount of tracer resulting in an increase in the rate of release of marker into the medium. Thus, by determining the rate at which marker is released into the medium, or in the alternative, by determining the amount of marker in the medium after a fixed period of time, and comparing such values with those obtained by an identical procedure using known amounts of analytes (standard analytes having known concentration), there can be obtained a measurement of the amount of analyte present in the sample.

The rate can be determined either kinetically be measuring the signal intensity increase with time, or by the end-point method, where the reaction is allowed to proceed for a fixed length of time, and it is then stopped (for example, by increasing the pH), and the color (or fluorescence, or luminescence, as the case may be) is measured. The higher the reaction rate, the stronger will be the signal at the end-point.

The sample volume which is used in the assay is selected so as to prevent a "run-away" rate for release of the marker, i.e., to provide a detectable rate of change with time. Thus, as the expected analyte concentration increases, the sample volume is decreased so as to provide for a detectable change in rate.

In an alternative embodiment, the binder may be supported on the walls of a tube, and in such a case, the bound and free portions of the tracer need not be separated from each other. More particularly, the sample containing or suspected of containing the analyte would be initially added to the tube containing the supported binder, followed by addition of sacs of the type hereinabove described. In such an assay, the tracer which becomes bound to the binder on the walls of the tube would not be free to move through the assay medium to contact the sacs, whereby the rate of release of marker from the sacs would be dependent upon the amount of free tracer in the assay medium.

In accordance with a further embodiment, the tracer of the type hereinabove described may be initially bound to binder supported on the walls of a tube. In such a case, the sample containing or suspected of containing the analyte, as well as the sacs of the type hereinabove described, may be simultaneously added to the tube. In such an embodiment, the analyte in the sample displaces tracer from the binder, with the amount of tracer displaced from the binder being directly proportional to the amount of analyte in the sample. In this embodiment, the tracer displaced from the binder comes into contact with the sacs to release a marker into the assay medium.

It may also be possible to employ a homogeneous assay in the case where the lysing agent used in the tracer is inactivated when the tracer is bound to the binder. Thus, for example, in an assay for digoxin which employs an antibody as a binder and a phospholipase as the enzymatic lysing agent bound to the ligand portion of the tracer, the phospholipsase is sterically hindered when bound to the antibody, whereby the bound tracer is not available for lysing sacs, whereas the unbound tracer is capable of lysing sacs to release from the sacs both detectable marker and lysing agent in an active form.

In accordance with another aspect of the invention, there is provided a reagent kit or package for accomplishing an assay for an analyte, which includes: (a) a tracer comprised of the analyte to be assayed or appropriate analog thereof conjugated to a sac lysing agent; and (b) sacs which include in the interior thereof sac lysing agent, in an inactive form, as well as a detectable marker, with, in some cases, the lysing agent and marker being the same substance. The sac lysing agent which forms a portion of the tracer, as well as the sac lysing agent within the sacs, is one which is capable of lysing the sacs included in the kit. The reagent kit or package may also include an appropriate binder, in supported or unsupported form, with such binder being a binder for both the tracer and the analyte to be assayed. The components of the kit may be included in the kit or package in separate containers; for example, vials; however, in some cases one or more of the components may be combined into a single vial. Similarly, as hereinabove described, the binder or the binder and tracer may be coated on the walls of a solid support. The kit may also include other components such as standards of the analyte (analyte samples having known concentrations of the analyte), known buffers, and the like.

The present invention is also applicable to providing of a first portion of the sacs used in the assay with lysing agent (in an inactive form) and a second portion of the sacs with a detectable marker to achieve amplification by a cascading effect. This alternative is of particular use when the marker and the lysing agent would be incompatible when placed in the same sac. Thus, at least a portion of the sacs includes a sac lysing agent, and at least a portion of the sacs includes a detectable marker, with a preferred embodiment being the use of sacs which include both the lysing agent and detectable marker.

The assay may be employed for determining analyte in a variety of body fluids; e.g., serum, urine, etc.

The invention will be further described with respect to the following examples; however, the scope of the invention is not to be limited thereby:

EXAMPLE I

Preparation of the Tracer: Phospholipase-Digoxigenin Conjugate

To 3-ketodigoxigenin carboxymethloxime (23.06 mg, 0.05 mmoles), add 0.6 ml dry DMF, followed by a solution of N-hydroxysuccinimide (5.75 mg) in dry DMF (0.1 ml) and dicylohexylcarbodiimide (10.1 mg) in dry DMF (0.1 ml). Mix overnight at 4° C., filter through glass wool, and add the clear solution to phospholipase C (5 mg) in 5 ml 0.1M tris-HCl (pH 8.0) at 0° C. Mix overnight at 0° C., centrifuge, and load the clear supernatant onto a Sephadex G-25 column, and elute the conjugate with the same buffer.

EXAMPLE II

Preparation of Liposomes Loaded with Inhibited Phospholipase and a Marker

To a 100 ml flask, add cholesterol (48 mg), distearoyl phosphatidyl choline (104 mg) and a mixture of diisopropyl ether (6.0 ml) and methanol (1.0 ml). Evaporate the solution on a rotary evaporator, and remove the last traces of organic solvent by high vacuum evaporation. Add a solution of phospholipase C (5 mg) in 6 ml 0.01M phosphate buffer, pH 7.5, containing EDTA (0.01M) and 4-methylumbelliferyl phosphate (0.05M). Swirl to disperse the lipids, and then sonicate for 8 minutes at room temperature. The loaded liposomes are separated from the free enzyme and the free marker by ultracentrifugation (three times at 75,000 g for 30 minutes).

EXAMPLE III

Assay Protocol

A. To anti-digoxin-coated tubes, add:
1. Digoxin standards or serum sample, 50 ul
2. Tracer: Digoxin-phosphalipase conjugate, 100 ul: Dissolve the conjugate in a buffer (0.01 phosphate, pH 7.5, 0.15M KCL and 5 mg/ml BSA), and adjust the concentration to about 0.1 ng/ml.
B. Incubate for 10–30 minutes at room temperature.
C. Decant, add 2 ml of buffer, and decant.
D. Add substrate. Liposomes suspended in tris-HCL buffer (tris-HCL, 50 mM, zinc chloride, 5mM, calcium chloride, 7 mM, BSA, 15 mg/ml, pH=7.3). Incubate for 5–10 minutes. Add one ml of 0.5M EDTA adjusted to pH 9. Read fluorescence (excitation at about 410 nm, fluorescence at 450 nm).

The present invention is particularly advantageous in that the assay has increased sensitivity. The cascading nature of the signal generating reaction results in a high amplification, whereby the present assay can be more sensitive than prior art non-isotope assays.

Numerous modifications and variations of the present invention are possible in light of the above teachings and, therefore, within the scope of the appended claims the invention may be practiced otherwise than as particularly described.

What is claimed is:

1. An assay for an analyte, comprising:
contacting tracer and analyte with a binder for at least the analyte, said tracer comprising a ligand coupled to a sac lysing agent, said ligand portion of the tracer becoming bound by one of the analyte and binder, whereby a portion of the tracer is bound to the binder; contacting unbound tracer with sacs, at least a portion of said sacs including in the interior thereof a detectable marker and at least a portion of the sacs including a sac lysing agent in an inactive form and which is active when released from the sacs; and determining marker released from the sacs as a measure of analyte.

2. The assay of claim 1 wherein at least a portion of the sacs include both the detectable marker and the lysing agent in the interior thereof.

3. The assay of claim 2 wherein the sacs are liposomes.

4. The assay of claim 3 wherein the lysing agent is an enzyme and the enzyme in the interior of the sacs is in an inactive form.

5. The assay of claim 1 wherein the binder is supported on a solid support.

6. The assay of claim 5 wherein the binder is a binder for both the analyte and tracer.

7. The assay of claim 6 wherein bound and free tracer portions are not separated prior to release of the marker whereby the assay is a homogeneous assay.

8. The assay of claim 5 wherein the detectable marker is a non-isotopic marker.

9. The assay of claim 2 wherein the analyte is a hapten.

10. The assay of claim 9 wherein the analyte is in a sample of a body fluid.

11. An assay for an analyte comprising:
contacting tracer and analyte with a binder for at least the analyte, said tracer comprising a ligand coupled to active liposome lysing agent comprising an enzyme, said ligand portion of the tracer becoming bound by one of the binder and analyte, whereby a portion of the tracer is bound by the binder;
contacting unbound tracer with liposomes containing in the interior therein a non-isotopic detectable marker and a liposome lysing agent comprising an enzyme in inactive form, said contacting with the liposomes being effected in the presence of an activating agent for the liposome lysing agent within the liposomes whereby detectable marker is released from the lysed liposomes and liposome lysing agent released from the liposomes is active for lysing additional liposomes to provide a cascading effect; and determining released marker as a measure of analyte.

12. The assay of claim 11 wherein the interior of the liposome includes a calcium dependent enzyme lysing agent and a calcium complexing agent to inactivate the enzyme lysing agent within the liposome, and the activating agent comprises calcium in an amount sufficient to activate released lysing agent.

13. The assay of claim 11 wherein the interior of the liposome includes an apo-enzyme and the activating agent is a coenzyme.

14. The assay of claim 11 wherein the binder is supported on a solid support.

15. The assay of claim 11 wherein the analyte is determined in a body fluid.

16. The assay of claim 15 wherein bound and free tracer portions are not separated prior to release of the marker whereby the assay is a homogeneous assay.

17. The assay of claim 16 wherein the analyte is a hapten.

18. A reagent kit for an assay for an analyte, comprising:
a package, said package containing (a) a tracer comprising a ligand coupled to a sac lysing agent; and (b) sacs, at least a portion of the sacs, containing in the interior thereof a sac lysing agent in an inactive form and at least a portion of the sacs containing in the interior thereof a detectable marker.

19. The kit of claim 18 wherein the sacs contain both the sac lysing agent, in inactive form, and the detectable marker in the interior thereof, said detectable marker being a non-isotopic marker.

20. The kit of claim 18 wherein the sacs are liposomes.

21. The kit of claim 20 wherein the package further contains a binder for at least the analyte, said ligand portion of the tracer being bound by the binder.

22. The kit of claim 21 wherein the lysing agent is an enzyme and the enzyme in the interior of the sacs is in an inactive form.

23. The kit of claim 22 wherein the enzyme lysing agent in the liposome is a calcium dependent enzyme and the interior of the liposome further contains a calcium complexing agent to inactivate the enzyme.

24. The kit of claim 18 wherein the package further contains a binder for the analyte, standard solutions of the analyte and an activating buffer for the sac lysing agent in the interior of the sacs.

* * * * *